United States Patent
Pujol

(10) Patent No.: US 10,046,136 B2
(45) Date of Patent: Aug. 14, 2018

(54) AUTOMATIC HUMIDITY CONTROL IN A PRESSURE SUPPORT SYSTEM

(75) Inventor: John Raymond Pujol, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1064 days.

(21) Appl. No.: 13/701,559

(22) PCT Filed: Apr. 27, 2011

(86) PCT No.: PCT/IB2011/051841
§ 371 (c)(1),
(2), (4) Date: Dec. 3, 2012

(87) PCT Pub. No.: WO2011/151741
PCT Pub. Date: Dec. 8, 2011

(65) Prior Publication Data
US 2013/0087143 A1    Apr. 11, 2013

Related U.S. Application Data

(60) Provisional application No. 61/351,324, filed on Jun. 4, 2010.

(51) Int. Cl.
| | | |
|---|---|---|
| *A61M 16/16* | (2006.01) | |
| *A61M 16/20* | (2006.01) | |
| *A61M 16/00* | (2006.01) | |

(52) U.S. Cl.
CPC ........ *A61M 16/16* (2013.01); *A61M 16/0069* (2014.02); *A61M 16/024* (2017.08);
(Continued)

(58) Field of Classification Search
CPC ...... A61M 2016/0039; A61M 16/0066; A61M 16/1075; A61M 16/109; A61M 16/1095;
(Continued)

(56) References Cited

U.S. PATENT DOCUMENTS

| | | | | |
|---|---|---|---|---|
| 4,722,334 A | * | 2/1988 | Blackmer | ................ A61D 7/04 |
| | | | | 128/203.16 |
| 5,148,802 A | | 9/1992 | Sanders | |

(Continued)

FOREIGN PATENT DOCUMENTS

| | | |
|---|---|---|
| CN | 101537221 A | 9/2009 |
| EP | 2098260 B1 | 4/2012 |

(Continued)

*Primary Examiner* — Tan-Uyen T Ho
*Assistant Examiner* — Joseph D Boecker
(74) *Attorney, Agent, or Firm* — Michael W. Haas

(57) ABSTRACT

A method of automatically controlling the humidity of a gas stream of a pressure support system (50) during use of the system is provided. The method includes receiving a first humidification level, and controlling operation of a humidifier (68) based on the first humidification level and at least one of: (i) one or more environmental parameters relating to environmental conditions around the pressure support system, (ii) one or more gas stream parameters relating to a gas stream output by the pressure support system to a patient circuit (56, 58), (iii) one or more respiratory demand parameters of a user of the pressure support system, and (iv) one or more operating parameters of the pressure support system that effect a flow rate that is generated by a pressure generating system (52, 60) of the pressure support system.

7 Claims, 2 Drawing Sheets

(52) U.S. Cl.
CPC ........ *A61M 16/161* (2014.02); *A61M 16/205* (2014.02); *A61M 16/0066* (2013.01); *A61M 2016/0039* (2013.01); *A61M 2205/3368* (2013.01)

(58) Field of Classification Search
CPC ................ A61M 16/16; A61M 16/161; A61M 2205/3368; A61M 2205/3372; A61M 2205/3653; A61M 2205/502
See application file for complete search history.

(56) References Cited

U.S. PATENT DOCUMENTS

| | | | |
|---|---|---|---|
| 5,313,937 | A | 5/1994 | Zdrojkowski |
| 5,433,193 | A | 7/1995 | Sanders |
| 5,632,269 | A | 5/1997 | Zdrojkowski |
| 5,803,065 | A | 9/1998 | Zdrojkowski |
| 6,029,664 | A | 2/2000 | Zdrojkowski |
| 6,435,180 | B1* | 8/2002 | Hewson ................ A61M 16/16 128/203.12 |
| 6,539,940 | B2 | 4/2003 | Zdrojkowski |
| 6,626,175 | B2 | 9/2003 | Jafari |
| 7,011,091 | B2 | 3/2006 | Hill |
| 8,640,696 | B2* | 2/2014 | Pujol et al. .............. 128/203.26 |
| 2001/0050080 | A1 | 12/2001 | Seakins |
| 2002/0112725 | A1* | 8/2002 | Thudor ................ A61M 16/16 128/204.18 |
| 2004/0016430 | A1* | 1/2004 | Makinson ............ A61M 16/10 128/203.12 |
| 2004/0182386 | A1* | 9/2004 | Meier .................. A61M 16/16 128/203.12 |
| 2006/0113690 | A1* | 6/2006 | Huddart ............ A61M 16/1075 261/129 |
| 2007/0169776 | A1 | 7/2007 | Kelper |
| 2007/0284361 | A1* | 12/2007 | Nadjafizadeh ........ A61M 16/16 219/442 |
| 2008/0105257 | A1* | 5/2008 | Klasek ............... A61M 16/0633 128/203.27 |
| 2008/0216832 | A1* | 9/2008 | Carter ............... A61M 16/0051 128/204.21 |
| 2008/0308100 | A1* | 12/2008 | Pujol .................. A61M 16/1075 128/203.14 |
| 2009/0223514 | A1* | 9/2009 | Smith ............... A61M 16/1075 128/203.14 |
| 2009/0301482 | A1* | 12/2009 | Burton .................. A61M 16/10 128/203.12 |
| 2010/0307495 | A1* | 12/2010 | Kepler ............... A61M 16/0057 128/203.26 |
| 2011/0120462 | A1* | 5/2011 | Tatkov ............... A61M 16/1075 128/203.14 |
| 2011/0125052 | A1* | 5/2011 | Davenport ........ A61M 16/0051 600/561 |
| 2011/0253136 | A1* | 10/2011 | Sweeney ............... A61M 16/16 128/203.12 |
| 2012/0125333 | A1* | 5/2012 | Bedford ................. A61M 16/06 128/203.25 |

FOREIGN PATENT DOCUMENTS

| | | |
|---|---|---|
| JP | H0838603 A | 2/1996 |
| JP | 2009213888 A | 9/2009 |
| JP | 2010517701 A | 5/2010 |
| WO | WO2007101298 A1 | 9/2007 |
| WO | WO2008076230 A2 | 6/2008 |
| WO | WO2009094532 A1 | 7/2009 |
| WO | WO2009084532 A1 | 9/2009 |
| WO | WO2009146484 A1 | 12/2009 |
| WO | WO2010016838 A1 | 2/2010 |

* cited by examiner

AUTOMATIC HUMIDITY CONTROL IN A PRESSURE SUPPORT SYSTEM

CROSS-REFERENCE TO RELATED APPLICATIONS

This patent application claims the priority benefit under 35 U.S.C. § 371 of international patent application no. PCT/IB2011/051841, filed Apr. 27, 2011, which claims the priority benefit under 35 U.S.C. § 119(e) of U.S. Provisional Application No. 61/351,324 filed on Jun. 4, 2010, the contents of which are herein incorporated by reference.

BACKGROUND OF THE INVENTION

1. Field of the Disclosure

The present invention relates to airway pressure support systems, and, more particularly, to an airway pressure support system in which the humidification of the gas stream delivered to the patient is automatically controlled.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

It is well known to treat sleep disordered breathing by applying a positive air pressure (PAP) to the patient's airway. This positive pressure effectively "splints" the airway, thereby maintaining an open passage to the lungs. In one type of PAP therapy, known as continuous positive air pressure (CPAP) the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

Humidifiers are frequently provided between or integral with a PAP machine and the user interface in order to humidify the otherwise relatively-dry compressed air generated by the PAP machine. Typically, humidifiers can be categorized as passover types or non-passover types. In a passover type of humidifier, water is contained in a reservoir that may or may not be heated. While the water is allowed to evaporate to produce vapor within the reservoir, breathing gas is passed over the surface of the water. Increased water vapor within the reservoir increases the capability to provide more humidity to the gas that is delivered to a user. In a non-passover type of humidifier, water is delivered into the gas stream via nebulization, atomization, vaporization or a combination thereof. Independent of the type of humidification used, in current positive airway pressure support systems the control of humidification is such that the output of humidity is relatively constant or on/off based on the user's demand.

SUMMARY OF THE INVENTION

In one embodiment, a method of automatically controlling the humidity of a gas stream of a pressure support system during use of the pressure support system is provided that includes receiving a first humidification level (e.g., a desired humidification level input by the user), and controlling operation of a humidifier of the pressure support system based on the first humidification level and at least one of: (i) one or more environmental parameters relating to environmental conditions around the pressure support system, (ii) one or more gas stream parameters relating to a gas stream output by the pressure support system to a patient circuit, (iii) one or more respiratory demand parameters of a user of the pressure support system, and (iv) one or more operating parameters of the pressure support system that effect a flow rate that is generated by a pressure generating system of the pressure support system.

In another embodiment, a pressure support system is provided that includes a pressure generating system, a humidifier structured to humidify a pressurized gas stream generated by the pressure generating system, a patient circuit operatively coupled to humidifier, and a controller operatively coupled to the pressure generating system and the humidifier. The controller is adapted to control the humidity of the gas stream output by the humidifier using the method just described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
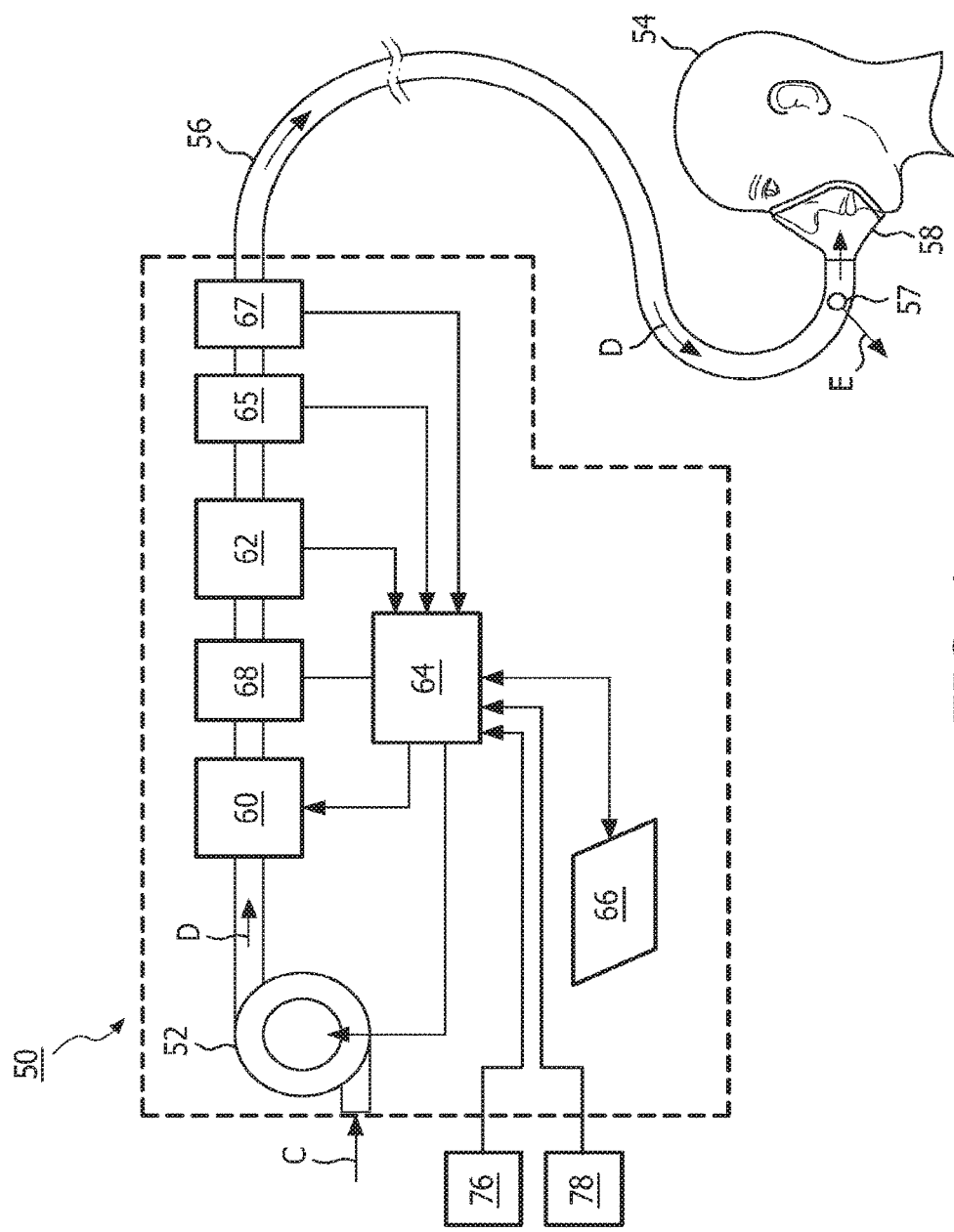
FIG. 1 is a schematic diagram of pressure support system according to one particular, non-limiting embodiment in which the present invention in its various embodiments may be implemented.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

DETAILED DESCRIPTION OF EXEMPLARY EMBODIMENTS

FIG. 1 is a schematic diagram of pressure support system 50 according to one particular, non-limiting embodiment in which the present invention in its various embodiments may be implemented. Referring to FIG. 1, pressure support system 50 includes gas flow generator 52, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of patient 54 at relatively higher and lower pressures, i.e., generally equal to or above ambient atmospheric pressure.

In an exemplary embodiment, gas flow generator 52 is capable of providing a flow of breathing gas ranging in pressure from 3-30 cm $H_2O$. The pressurized flow of breathing gas, generally indicated by arrow D from gas flow generator 52, is delivered via delivery conduit 56 to breathing mask or patient interface 58 of any known construction, which is typically worn by or otherwise attached to patient 54 to communicate the flow of breathing gas to the airway of patient 54. Delivery conduit 56 and patient interface device 58 are typically collectively referred to as a patient circuit.

Pressure support system 50 shown in FIG. 1 is what is known as a single-limb system, meaning that the patient circuit includes only delivery conduit 56 connecting patient 54 to pressure support system 50. As such, exhaust vent 57 is provided in delivery conduit 56 for venting exhaled gasses from the system as indicated by arrow E. It should be noted that exhaust vent 57 can be provided at other locations in addition to or instead of in delivery conduit 56, such as in patient interface device 58. It should also be understood that exhaust vent 57 can have a wide variety of configurations depending on the desired manner in which gas is to be vented from pressure support system 50.

The present invention also contemplates that pressure support system 50 can be a two-limb system, having a delivery conduit and an exhaust conduit connected to patient 54. In a two-limb system (also referred to as a dual-limb system), the exhaust conduit carries exhaust gas from patient 54 and includes an exhaust valve at the end distal from patient 54. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 58 is a nasal/oral mask. It is to be understood, however, that patient interface 58 can include a nasal mask, nasal pillows, a tracheal tube, an endotracheal tube, or any other device that provides a suitable gas flow communicating function. Also, for purposes of the present invention, the phrase "patient interface" can include delivery conduit 56 and any other structures that connect the source of pressurized breathing gas to patient 54.

In the illustrated embodiment, pressure support system 50 includes a pressure controller in the form of valve 60 provided in delivery conduit 56. Valve 60 controls the pressure of the flow of breathing gas from flow generator 52 that is delivered to patient 54. For present purposes, flow generator 52 and valve 60 are collectively referred to as a pressure generating system because they act in concert to control the pressure and/or flow of gas delivered to patient 54. However, it should be apparent that other techniques for controlling the pressure of the gas delivered to patient 54, such as varying the blower speed of flow generator 52, either alone or in combination with a pressure control valve, are contemplated by the present invention. Thus, valve 60 is optional depending on the technique used to control the pressure of the flow of breathing gas delivered to patient 54. If valve 60 is eliminated, the pressure generating system corresponds to flow generator 52 alone, and the pressure of gas in the patient circuit is controlled, for example, by controlling the motor speed of flow generator 52.

Pressure support system 50 further includes flow sensor 62 that measures the flow of the breathing gas within delivery conduit 56. In the particular embodiment shown in FIG. 1, flow sensor 62 is interposed in line with delivery conduit 56, most preferably downstream of valve 60. Flow sensor 62 generates a flow signal, $Q_{measured}$, that is provided to controller 64 and is used by controller 64 to determine the flow of gas at patient 54 ($Q_{patient}$).

Techniques for calculating $Q_{patient}$ based on $Q_{measured}$ are well known, and take into consideration the pressure drop of the patient circuit, known leaks from the system, i.e., the intentional exhausting of gas from the circuit as indicated by arrow E in FIG. 1, and unknown leaks from the system, such a leaks at the mask/patient interface. The present invention contemplates using any known or hereafter developed technique for calculating leak flow $Q_{leak}$, and using this determination in calculating $Q_{patient}$ based on $Q_{measured}$. Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 54 are contemplated by the present invention, such as, without limitation, measuring the flow directly at patient 54 or at other locations along delivery conduit 56, measuring patient flow based on the operation of flow generator 52, and measuring patient flow using a flow sensor upstream of valve 60.

$Q_{patient}$, which, as noted above, is the flow rate of the breathing gas that is actually received by patient 54, is one example of a parameter relating to the respiratory demand of patient 54. Other patient respiratory demand parameters that may be used in the present invention, as described in greater detail below, include, without limitation, tidal volume and respiratory rate. As known in the art, tidal volume can be determined by integrating flow rate through portions of the respiratory cycle.

In the illustrated embodiment, pressure support system 50 also includes temperature sensor 65 operatively coupled to delivery conduit 56 for detecting the temperature of the gas stream output by pressure support system 50, and humidity sensor 67 operatively coupled to delivery conduit 56 for detecting the humidity of the gas stream output by pressure support system 50. Temperature sensor 65 and humidity sensor 67 are each operatively coupled to controller 64. In the embodiment shown, temperature sensor 65 and humidity sensor 67 are provided within the main housing of pressure support system 50. Alternatively, either or both of temperature sensor 65 and humidity sensor 67 may be provided in or coupled to the patient circuit.

Controller 64 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 50, including automatically controlling humidity as described in greater detail herein.

Input/output device 66 is provided for setting various parameters used by pressure support system 50, as well as for displaying and outputting information and data to a user, such as a clinician or caregiver. Input/output device 66 may be used by a user of pressure support system 50 to establish a set/desired humidification level, the significance of which is described elsewhere herein.

In the illustrated embodiment, pressure support system 50 also includes humidifier 68 provided in the main housing of pressure support system 50. Alternatively, humidifier 68 may be separate from and located external to the main housing. Humidifier 68 is controlled by controller 64. Humidifier 68 further improves comfort by providing moisture in the supplied gas. In the exemplary embodiment, humidifier 68 is a passover type humidifier. U.S. Patent Application Publication No. 2007/0169776, incorporated herein by reference in its entirety, discloses an exemplary humidifier device suitable for use in the present invention. Humidifier devices having alternative designs, such as a non-passover type humidifier that employs nebulization, atomization, vaporization or a combination thereof, may also be used.

In the illustrated, non-limiting embodiment of the present invention, pressure support system 50 essentially functions as a CPAP pressure support system, and, therefore, includes all of the capabilities necessary in such systems in order to provide appropriate CPAP pressure levels to patient 54. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Finally, in the illustrated embodiment, pressure support system 50 also includes ambient temperature sensor 76 and ambient humidity sensor 78. Both ambient temperature sensor 76 and ambient humidity sensor 78 are operatively coupled to controller 64. Ambient temperature sensor 76 measures the ambient temperature around pressure support system 50, and thus the temperature of the gas entering pressure support system 50, and provides that information to controller 64. Ambient humidity sensor 78 measures the ambient humidity around pressure support system 50, and thus the humidity of the gas entering pressure support system 50, and provides that information to controller 64. In the illustrated embodiment, ambient temperature sensor 76 and ambient humidity sensor 78 are located adjacent to the inlet of gas flow generator 52.

As noted elsewhere herein, according to the methodology of the present invention (implemented in software executable by controller 64 for controlling pressure support system 50), pressure support system 50 automatically controls the humidity level of the breathing gas that is delivered to the patient circuit based on: (i) a set/desired humidification level specified by the user (the level may, for example, be expressed as a particular relative humidity such as 60% or 80%, or may be expressed on a scale such as low, medium, high or 1, 2, 3, 4) and (ii) one or more other parameters described in greater detail herein. More specifically, the other parameters may include any of the following, alone or in various combinations: (i) certain measured or estimated environmental conditions around pressure support system 50, such as, without limitation, ambient temperature, ambient humidity, and/or barometric pressure; (ii) certain measured or estimated gas stream conditions, such as, without limitation, the temperature and/or humidity of the gas stream output by pressure support system 50; (iii) certain measured or estimated user respiratory demand parameters, such as flow rate, tidal volume and/or respiration rate, and (iv) certain operating parameters of pressure support system 50 that effect the flow rate of breathing gas that is output by pressure support system 50, such as the pressure level of the breathing gas generated by the pressure generating system that includes flow generator 52. As these parameters change, the amount of humidification delivered to the gas stream is increased or decreased in order to attempt to maintain a consistent amount of humidification in the gas that is actually delivered to the user.

As described in greater detail below, ambient temperature may be directly measured by ambient temperature sensor 76 (as in the illustrated embodiment of FIG. 1), or, alternatively, may be estimated or derived based on other data obtained by pressure support system 50. Similarly, ambient humidity may be directly measured by ambient humidity sensor 78 (as in the illustrated embodiment of FIG. 1), or, alternatively, may be estimated or derived based on other data obtained by pressure support system 50. Similarly, gas stream temperature may be directly measured by temperature sensor 65 (as in the illustrated embodiment of FIG. 1), or, alternatively, may be estimated or derived based on other data obtained by pressure support system 50, and the humidity of the gas stream output by pressure support system 50 may be directly measured by humidity sensor 67 (as in the illustrated embodiment of FIG. 1), or, alternatively, may be estimated or derived based on other data obtained by pressure support system 50.

Figure 2:
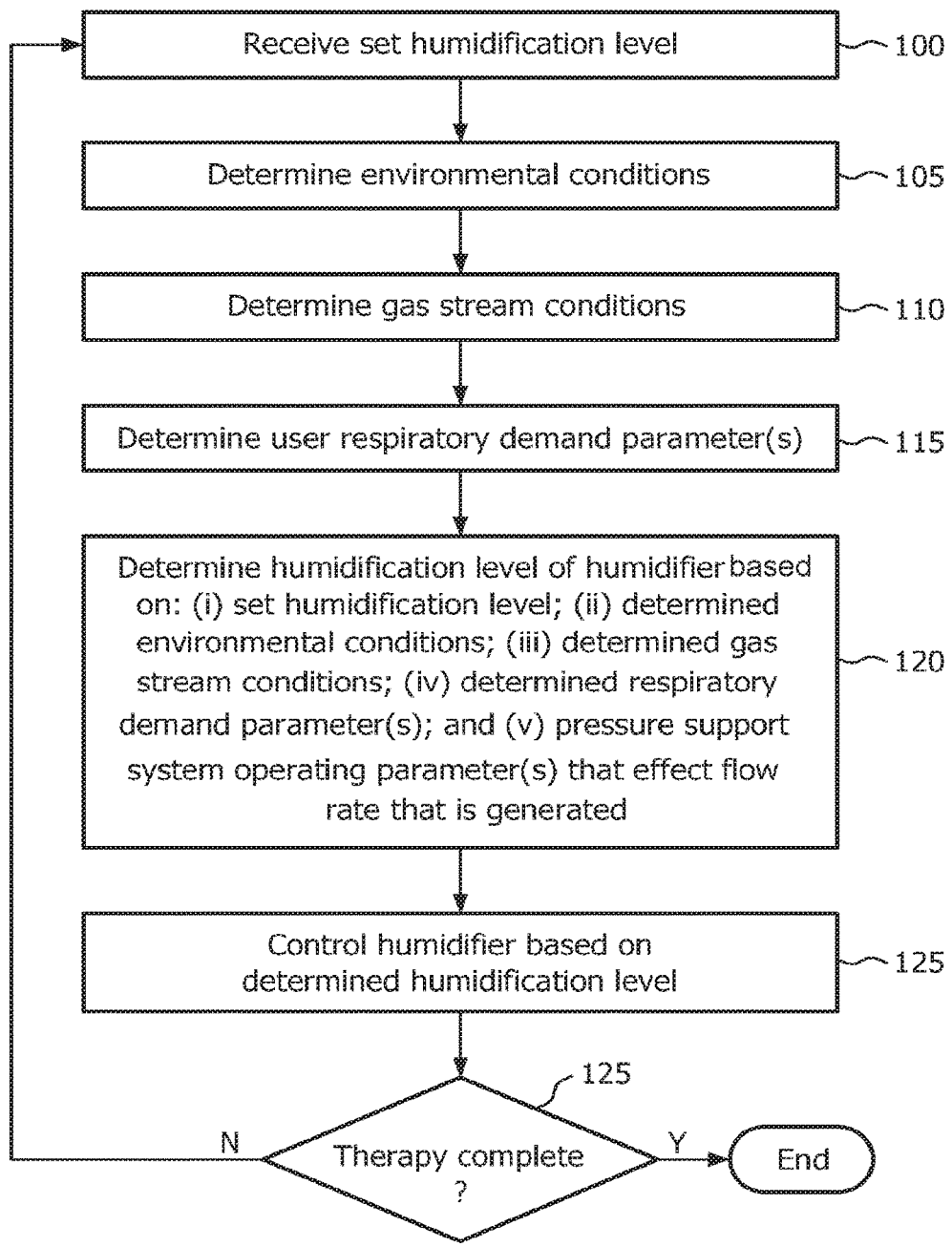
FIG. 2 is a flowchart showing a method of automatically controlling the humidity level of the breathing gas that is delivered to a patient circuit of a pressure support system according to one particular, non-limiting embodiment of the invention.

FIG. 2 is a flowchart showing a method of automatically controlling the humidity level of the breathing gas that is delivered to the patient circuit according to one particular, non-limiting embodiment of the invention. The method shown in FIG. 2 may be implemented in the exemplary pressure support system 50 shown in FIG. 1 (or in another suitable pressure support system) through appropriate programming of controller 64. For illustrative purposes, the method will be described herein as implemented in the pressure support system 50. In addition, while the method controlling the humidity level shown in FIG. 2 may be performed at the initiation of therapy, it is also to be understood that it may be performed periodically throughout a therapy session at some desired humidity update rate.

The method begins at step 100, wherein controller 64 receives the set humidification level. As discussed elsewhere herein, this may be input by the user using, for example, input/output device 66. Next, at step 105, one or more environmental conditions, such as the ambient temperature and the ambient humidity around pressure support system 50, are determined. In the exemplary embodiment, the ambient temperature is measured by ambient temperature sensor 76 and the ambient humidity is measured by ambient humidity sensor 78. Alternatively, ambient temperature sensor 76 and ambient humidity sensor 78 may be omitted, and the ambient temperature and the ambient humidity may be estimated or derived from the operating parameters of pressure support system 50 (e.g., pressure level) and/or from data that is measured/sensed by pressure support system 50 (such as, without limitation, temperature and humidity as measured by temperature sensor 65 and humidity sensor 67) using any of a number of known methods of back estimation/derivation.

Next, at step 110, certain gas stream conditions, such as temperature and humidity, relating to the gas output by pressure support system 50 and entering delivery conduit 56 are determined. In the exemplary embodiment, gas stream temperature is measured by temperature sensor 65 and gas stream humidity is measured by humidity sensor 67. Alternatively, temperature sensor 65 and humidity sensor 67 may be omitted, and the gas stream temperature and the gas stream humidity may be estimated or derived from the operating parameters of pressure support system 50 and the ambient temperature measured by ambient temperature sensor 76 and/or ambient humidity as measured by ambient humidity sensor 78 using any of a number of known methods of feed forward estimation/derivation. One such suitable method is described in United States Patent Application Publication No. 2008/0308100, the disclosure of which is incorporated herein by reference.

Then, as step 115, certain user respiratory demand parameters, such as flow rate, tidal volume and/or respiration rate, are measured or derived/estimated. For example, flow rate of patient 54 ($Q_{patient}$) may be determined by controller 64 based on the output of flow sensor 62 ($Q_{measured}$) in the manner described elsewhere wherein. Tidal volume of patient 54 may also be determined by controller 64 by integrating the flow rate over time. Other methods of determining flow rate and/or tidal volume are also contemplated and are within the scope of the present invention.

Next, at step 120 in the illustrated embodiment, a humidification level for humidifier 68 is determined based on (i) the set/desired humidification level specified by the user; (ii) the determined environmental conditions around pressure support system 50; (iii) the determined gas stream conditions; (iv) the determined user respiratory demand parameters, and (v) certain operating parameters of the pressure support system 50 that effect the flow rate of breathing gas that is output by pressure support system 50. In the exemplary embodiment, the humidification level for humidifier 68 that is determined/calculated is the humidity level of the gas at the output of humidifier 68 that is required to cause the humidity level of the gas ultimately delivered to the airway of patient 54 to be substantially equal to the set humidification level (step 100). In other words, controller 64 will control humidifier 68 to add more or less moisture to the breathing gas so that the set humidification level is actually delivered to patient 54 taking into account each of the parameters/variables (ii)-(v) listed above. Knowing the properties of air and water and using the data of (i)-(v) above, that humidification level may be determined/calculated in a number of different ways that are within the ordinary skill in the art (without undue experimentation). Thus, such methods will not be discussed in great detail herein.

In one example methodology, that humidification level may be determined/calculated in the following manner. First, based on the desired humidification level, the properties of the patient circuit, the environmental conditions and the flow rate delivered to the patient (patient demand), the humidity level that must be output by humidifier 68 so that the humidity level of the gas ultimately delivered to the airway of patient 54 will be the desired humidification level may be determined using known methods. Then, based on that humidity level, the system may be controlled to achieve that output level at humidifier 68 as follows. Starting with a known environmental temperature and absolute and/or relative humidity of the gas stream C in FIG. 1, it is known that that temperature will rise a determinable amount as the gas is compressed by gas flow generator 52. In addition, a known amount of energy may be selectively supplied to humidifier 68. Thus, knowing the temperature and absolute and/or relative humidity of the gas that will be supplied to humidifier 68 along with the efficiency of humidifier 68, the amount of energy that must be supplied to humidifier 68 to achieve the predefined humidity output level of humidifier 68 may be determined and that energy level may be applied to humidifier 68.

Following step 120, the method proceeds to step 125, wherein humidifier 68 is controlled by controller 64 based on the determined humidification level. In the exemplary embodiment, wherein humidifier 68 is a passover type humidifier, controller 64 sets the temperature of humidifier 68 to a level that will achieve the determined humidification level. If another type of humidifier is used, such as a nebulizing/atomizing humidifier, controller 64 will control the amount of moisture that is added through nebulization/atomization in order to achieve the determined humidification level. Then, at step 130, a determination is made as to whether therapy is complete. If the answer is yes, then the method ends. If the answer is no, then the method returns to step 100 and repeats.

Numerous variations of how to determine the humidification level (step 120) are also possible. For example, various combinations of one or more of the parameters/variables (ii)-(v) may be employed. In one particular alternative embodiment, the humidification level is determined based on just the set/desired humidification level and certain determined user respiratory demand parameters, such as flow rate, tidal volume and/or respiratory rate. As the user demand changes, the amount of humidity delivered to the gas stream is varied and controlled on a real time basis. In another particular alternative embodiment, the humidification level is determined based on the set/desired humidification level, certain determined user respiratory demand parameters, such as flow rate, tidal volume and/or respiratory rate, and certain operating parameters of the pressure support system 50 that effect the flow rate of breathing gas that is output by pressure support system 50, such as pressure level. In this embodiment, as the user demand and/or system operating parameters change, the amount of humidity delivered to the gas stream is varied and controlled on a real time basis. Still other variations are possible within the scope of the present invention and will be apparent to those of skill in the art.

In one particular embodiment, the real time control and variation of the amount of humidity delivered to the gas stream is done on a breath to breath basis. Alternatively, data relating to multiple breaths may be averaged over time and the real time control and variation of the amount of humidity delivered to the gas stream may be based thereon.

Additionally, trending of humidification loading along with predicting can be accomplished using this invention. More specifically, a patient's flow rate, tidal volume and/or respiratory rate can vary during the various stages of sleep and/or during/based on the type of therapy being administered (e.g., in certain types of therapy, pressure is automatically adjusted up and down). By monitoring/knowing the current sleep stage, therapy being administered and/or the respiratory behavior of the patient and by considering past humidification data, the desired humidification level for the patient can be predicted/anticipated and pressure support system 50 can be controlled to go to that level.

Thus, the present invention provides a system and method of automatic and variable humidification that provides a consistent amount of humidification to the gas stream and hence to the user. One advantage of the system and method of the present invention is that it optimizes the amount of humidification in the gas stream dependent on the desired humidification level and one or more of the user's demand, environmental conditions, gas stream conditions and current operating parameters of the pressure support system. By optimizing the amount of humidification in the gas stream, water used for humidification can be conserved. In addition, unnecessary amounts of water vapor in the gas stream that can condense within the patient circuit can be reduced and/or eliminated.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of automatically controlling a humidity of a gas stream of a pressure support system during use of the pressure support system by a user, the pressure support system comprising a patient circuit, a humidifier, and a controller, the method comprising:
   receiving, by the controller, a first humidification level, the first humidification level being a desired humidification level to be delivered to an airway of the user through the patient circuit;
   determining, by the controller:
      (i) one or more parameters indicating the user's actual demand for respiratory gas during a breath, the one or more parameters including a tidal volume of the user during the breath and a respiratory rate of the user during the breath,
      (ii) an ambient temperature, and
      (iii) an ambient humidity, wherein the one or more parameters include parameters of gas actually received by the user;
   determining, by the controller, a second humidification level of a breathing gas to be output by the humidifier, wherein determining the second humidification is based on the first humidification level, a property of the patient circuit, the ambient temperature, the ambient humidity, and the one or more parameters indicating the user's actual demand for respiratory gas, and wherein the second humidification level is a level that will cause the breathing gas to have a humidity that is substantially equal to the first humidification level after the breathing gas passes through the patient circuit and is delivered to the airway of the user; and
   controlling, by the controller, operation of the humidifier to cause it to output the breathing gas with a humidity equal to the second humidification level.

2. The method according to claim 1, wherein the controlling includes controlling operation of the humidifier by determining an amount of energy to be provided to the humidifier based on the ambient temperature and the ambient humidity, and providing the amount of energy to the humidifier.

3. The method according to claim 1, wherein determining the one or more parameters indicating the user's actual demand for respiratory gas comprises measuring or estimating the one or more parameters indicating the user's actual demand for respiratory gas.

4. The method according to claim 1, wherein the controlling operation of the humidifier is based on one or more operating parameters of the pressure support system that affect a flow rate that is generated by a pressure generating system of the pressure support system.

5. A pressure support system, comprising:
   a pressure generating system structured to generate a pressurized gas stream;
   a humidifier structured to humidify the pressurized gas stream;
   a patient circuit operatively coupled to the humidifier; and a controller operatively coupled to the pressure generating system and the humidifier, the controller being adapted to:
  receive a first humidification level, the first humidification level being a desired humidification level to be delivered to an airway of a user through the patient circuit;
  determine:
    (i) one or more parameters indicating the user's actual demand for respiratory gas during a breath, the one or more parameters including a tidal volume of the user during the breath and a respiratory rate of the user during the breath,
    (ii) an ambient temperature, and
    (iii) an ambient humidity, wherein the one or more parameters include parameters of gas actually received by the user;
  determine a second humidification level of a breathing gas to be output by the humidifier, wherein determining the second humidification level is based on the first humidification level, a property of the patient circuit, the ambient temperature, the ambient humidity, and the one or more parameters indicating the user's actual demand for respiratory gas, and wherein the second humidification level is a level that will cause the breathing gas to have a humidity that is substantially equal to the first humidification level after the breathing gas passes through the patient circuit and is delivered to the airway of the user; and
  control operation of the humidifier to cause it to output the breathing gas with a humidity equal to the second humidification level.

6. The pressure support system according to claim 5, wherein the controller is adapted to control operation of the humidifier by determining an amount of energy to be provided to the humidifier based on the ambient temperature and the ambient humidity, and provide the amount of energy to the humidifier.

7. The pressure support system according to claim 5, wherein the one or more parameters indicating the user's actual demand for respiratory gas are either measured using one or more sensors or estimated by the controller.

* * * * *